US006376188B1

(12) United States Patent
Halling et al.

(10) Patent No.: US 6,376,188 B1
(45) Date of Patent: *Apr. 23, 2002

(54) METHOD AND PROBE SET FOR DETECTING CANCER

(75) Inventors: Kevin C. Halling; Robert B. Jenkins, both of Rochester, MN (US); Walter King, Wheaton, IL (US); Irina A. Sokolova, Lombard, IL (US); Steven A. Seelig, Naperville, IL (US)

(73) Assignees: Mayo Foundation for Medical Education and Research, Rochester, MN (US); Vysis, Inc., Downers Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,173

(22) Filed: Jul. 21, 2000

Related U.S. Application Data

(63) Continuation of application No. 09/264,149, filed on Mar. 5, 1999, now Pat. No. 6,174,681.

(51) Int. Cl.$^7$ .............................. C12Q 1/68; C12N 5/00; G01N 33/50; C07H 21/04
(52) U.S. Cl. ........................ 435/6; 435/325; 435/287.1; 435/288.3; 536/23.1; 536/24.3; 536/24.31
(58) Field of Search ....................... 435/6, 810, 325, 435/208.1, 288.3; 536/23.1, 24.3, 24.31

(56) References Cited

U.S. PATENT DOCUMENTS

| | | |
|---|---|---|
| 5,028,525 A | 7/1991 | Gray et al. |
| 5,447,841 A | 9/1995 | Gray et al. |
| 5,491,224 A | 2/1996 | Bittner et al. |
| 5,624,819 A | 4/1997 | Skolnick et al. |
| 5,665,549 A | 9/1997 | Pinkel et al. |
| 5,756,696 A | 5/1998 | Gray et al. |
| 5,776,688 A | 7/1998 | Bittner et al. |
| 5,856,089 A | 1/1999 | Wang et al. |

FOREIGN PATENT DOCUMENTS

| | | |
|---|---|---|
| EP | 1 035 215 | 9/2000 |
| WO | WO 95/13398 | 5/1995 |
| WO | WO 98/38333 | 9/1998 |

OTHER PUBLICATIONS

Ahmann et al., *Cancer Genet. Cytogenet.*, 1998, 101:7–11.
Alcaraz et al., *Cancer Res.*, 1994, 54:3998–4002.
Cajulis et al., *Anal. Quant. Cytol. Histol.*, 1994, 16(1):1–10.
Cajulis et al., *Diagn. Cytopathol.*, 1995, 13(3):214–224.
Ellis et al., *Urology*, 1997, 50(6):882–887.
Florentine et al., *Cancer*, 1997, 81(5):299–308.
Halling et al., *J. Urol.*, 2000, 164(5):1768–1775.
Landman et al., *Urology*, 1998, 52(3):398–402.
Li et al., *Am. J. Pathol.*, 1996, 149(1):229–235.
Macoska et al., *Cancer Res.*, 1994, 54:3824–3830.
Mao et al., *Science*, 1996, 271(5249):659–662.
Matsuyama et al., *Cancer Genet. Cytogenet.*, 1994, 77(2):118–124.
Mayfield et al., *Brit. J. Urology*, 1998, 82(6):825–828.
Meloni et al., *Cancer Genet. Cytogenet.*, 1993, 71:105–118.
Messing et al., *Urology*, 1995, 45(3):387–397.
Moore et al., *Environ. Mol. Mutagenesis*, 1993, 22:130–137.
Nath et al., *Biotechnic Histochem.*, 1998, 73(1):6–22.
Persons et al., *Clin. Cancer Res.*, 1996, 2:883–888.
Pycha et al., *J. Urol.*, 1997, 157(6):2116–2119.
Ramaekers et al., *Ann. N.Y. Acad. Sci.*, 1993, 677:199–213.
Sauter et al., *Cancer Genet. Cytogenet.*, 1995, 82(2):163–169.
Sauter et al., *Urological Res.*, 1997, 25(Supp. 1):S37–S43.
Sokolova et al., *J. Mol. Diag.*, 2000, 2(3):116–123.
Waldman et al., *Cancer Res.*, 1991, 51(14):3807–3813.
Wheeless et al., *Cytometry*, 1994, 17(4):319–326.
Yokogi et al., *Brit. J. Urology*, 1996, 78(5):699–703.
Zhang et al., *Environ. Health Perspect.*, 1996, 104(Suppl. 6):1325–1329.
Zhang et al., *Clin. Cancer Res.*, 1997, 3(12):2317–2328.
Zojer et al., *Brit. J. Urology*, 1997, 75(3):403–407.
Zojer et al., *Brit. J. Urology*, 1998, 77(8):1337–1342.
Sauter et al., "Chromosome –9 Loss Detected by Fluorescence in situ Hybridization in Bladder Cancer," *Int. J. Cancer (Pred. Oncol.)*1995, 64:99–103.

*Primary Examiner*—Stephanie W. Zitomer
(74) *Attorney, Agent, or Firm*—Fish & Richardson P.C.

(57) ABSTRACT

Methods for detecting cancer that include hybridizing a set of chromosomal probes to a biological sample obtained from a patient, and identifying if aneusomic cells are present in a selected subset of cells obtained from the biological sample are described. A set of chromosomal probes and kits for detecting cancer that include sets of chromosomal probes, are also described.

17 Claims, No Drawings

METHOD AND PROBE SET FOR DETECTING CANCER

This application is a continuation of U.S. Ser. No. 09/264,149, filed Mar. 5, 1999, now U.S. Pat. No. 6,174,681.

TECHNICAL FIELD

The invention relates to detecting cancer.

BACKGROUND OF THE INVENTION

Bladder cancer represents the fifth most common neoplasm and the twelfth leading cause of cancer death in the United States, where over 53,000 new cases are diagnosed each year. Over 95% of bladder cancer cases in the United States are transitional cell carcinoma (TCC, sometimes referred to as urothelial cell carcinoma). Tumor stage is the best predictor of prognosis for patients with bladder cancer. Bladder cancer is staged according to the depth of invasion of the tumor and whether or not there are lymph node or distant metastases. Non-invasive papillary tumors (the most common and least aggressive type of bladder tumor) are referred to as stage pTa tumors. "Flat" TCC, more commonly referred to as "carcinoma in situ" (CIS) is a more aggressive but less common tumor that is associated with a high rate of progression to invasive disease. CIS is assigned a stage of pTIS. Tumors that have invaded through the basement membrane of the epithelium into the underlying lamina propria are assigned a stage of pT1. A tumor that has invaded the muscle of the bladder is a stage pT2 tumor. Invasion through the muscle into the tissue surrounding the bladder is a pT3 tumor. Invasion into surrounding organs is a pT4 tumor. The term "superficial" bladder cancer refers to pTa, pTIS, and pT1 tumors. Muscle-invasive bladder cancer refers to pT2, pT3, and pT4 tumors.

Approximately 80% of bladder cancer cases present as "superficial" bladder cancer and the remaining 20% as muscle-invasive bladder cancer. Patients with "superficial" bladder cancer do not require cystectomy (i.e. removal of the bladder) but have a high risk of tumor recurrence, and are monitored for tumor recurrence and/progression on a regular basis (usually every 3 months for the first 2 years, every 6 months for the next 2 years, and every year thereafter). Treatment for superficial bladder cancer generally consists of surgical removal of papillary tumors and treatment of CIS with Bacillus-Calmette Guerin (BCG). Patients with muscle invasive disease are treated by cystectomy and have a relatively poor prognosis compared to patients with "superficial" bladder cancer. Unfortunately, 80–90% of patients with muscle invasive bladder cancer initially present with muscle invasive disease. A large share of the estimated 10,000 deaths per year from bladder cancer is accounted for by this group of patients. The fact that many patients with advanced bladder cancer present that way suggests that screening programs that detect bladder cancer at earlier stages may help reduce the overall mortality from the disease. In fact, at least two large screening studies suggest that screening does help identify bladder cancer at earlier stages. Messing et al., *Urology.* 45:387–396, 1995; and Mayfield and Whelan, *Br. J. Urol.*, 82(6):825–828, 1998.

Cystoscopy and urine cytology have been the mainstays for bladder cancer detection over the past several decades. Several studies, however, have shown that cytology has a disappointingly low sensitivity for bladder cancer detection. Mao et al.,*Science,* 271:659–662, 1996; Ellis et al., *Urology,* 50:882–887, 1997; and Landman et al., *Urology,* 52:398–402, 1998. For this reason, there has been great interest in the development of new assays that have increased sensitivity for the detection of bladder cancer. Examples of new assays that have been developed for bladder cancer detection include tests that detect bladder tumor antigens (BT test, C. R. Bard, Inc., Murrayhill, N.J.), nuclear matrix protein (NMP-22 test), and fibrin degradation products (FDP test), etc.; tests that detect increased telomerase activity (usually associated with malignance); or tests that detect genetic alterations in urinary cells and bladder washings (e.g. fluorescence in situ hybridization (FISH) and microsatellite analysis). Although FISH analysis may be more sensitive than other detection methods, large numbers of cells must be counted, and consequently, the analysis is time consuming and costly. Therefore, a need exists for a rapid method of detecting cancer that maintains adequate sensitivity.

SUMMARY OF THE INVENTION

The invention is based, in part, on the discovery that a rapid, sensitive method for detecting cancer can be based on the presence of aneusomic cells in a selected subset of cells from a biological sample. Selection of a subset of cells to be evaluated for chromosomal anomalies reduces the number of cells to be analyzed, allowing analysis to be performed in a rapid manner while maintaining, and even improving, sensitivity. The invention also provides a set of chromosomal probes selected to provide the optimal sensitivity in FISH analysis and kits for detecting cancer that include sets of chromosomal probes.

In one aspect, the invention features a method of screening for cancer in a subject. The method includes the steps of hybridizing a set of chromosomal probes to a biological sample from the subject; selecting cells from the biological sample; determining the presence or absence of aneusomic cells in the selected cells; and correlating the presence of aneusomic cells in the selected cells with cancer in the subject. The biological sample can be urine, blood, cerebrospinal fluid, pleural fluid, sputum, peritoneal fluid, bladder washings, oral washings, tissue samples, touch preps, or fine need aspirates, and can be concentrated prior to use. Urine is a particularly useful biological sample. The cells can be selected by nuclear morphology including nucleus size and shape. Nuclear morphology can be assessed by 4,6-diamidine-2-phenylindole dihydrochloride (DAPI) staining. The method is useful for detecting cancers such as bladder cancer, lung cancer, breast cancer, ovarian cancer, prostate cancer, colorectal cancer, renal cancer, and leukemia. The method is particularly useful for detecting bladder cancer.

The set of chromosomal probes includes at least three chromosomal probes. The set can include at least one centromeric probe or at least one locus specific probe. Suitable centromeric chromosomal probes include probes to chromosomes 3, 7, 8, 11, 15, 17, 18, and Y. A suitable locus specific probe includes a probe to the 9p21 region of chromosome 9. For example, the set can include centromeric chromosomal probes 3, 7, and 17, and further can include locus specific probe 9p21. The chromosomal probes can be fluorescently labeled.

The invention also features sets of chromosomal probes and kits for detecting cancer that include sets of chromosomal probes, that include centromeric probes to chromosomes 3, 7, and 17, and further can include a locus-specific probe such as 9p21. The chromosomal probes can be fluorescently labeled.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention advantageously provides a rapid, sensitive method for detecting cancer, and can be used to screen subjects at risk for cancer, including solid tumors and leukemias, or to monitor patients diagnosed with cancer for tumor recurrence. For example, subjects at risk for bladder cancer, lung cancer, breast cancer, ovarian cancer, prostate cancer, colorectal cancer, head and neck cancer, renal cancer, or leukemia can be screened or monitored for recurrence. In general, a set of chromosomal probes is hybridized to cells (from urine or other biological sample) on a slide. The cells on the slide are then visually scanned at a relatively low power (e.g. 200–400×) for morphologic features strongly suggestive of malignancy (e.g. increased nuclear size or irregular nuclear shape). The nuclei of the cytologically abnormal cells are then examined for chromosomal abnormalities by switching the objective to a higher power (e.g. 600–1000×) and "flipping" the filters to determine if the cell is aneusomic or not. Use of this process markedly reduces the time spent assessing cells that have a low probability of being neoplastic and allows the examiner to focus their efforts on the cells that have a much higher probability of being neoplastic and showing aneusomy.

In Situ Hybridization

The presence or absence of aneusomic cells is determined by in situ hybridization. "Aneusomic cells" are cells having an abnormal number of chromosomes or having chromosomal structural alterations such as hemizygous or homozygous loss of a specific chromosomal region. Typically, aneusomic cells having one or more chromosomal gains, i.e., three or more copies of any given chromosome, are considered test positive in the methods described herein, although cells exhibiting monosomy and nullisomy also may be considered test positive under certain circumstances. In general, in situ hybridization includes the steps of fixing a biological sample, hybridizing a chromosomal probe to target DNA contained within the fixed biological sample, washing to remove non-specific binding, and detecting the hybridized probe.

A "biological sample" is a sample that contains cells or cellular material. Typically, the biological sample is concentrated prior to hybridization to increase cell density. Non-limiting examples of biological samples include urine, blood, cerebrospinal fluid (CSF), pleural fluid, sputum, and peritoneal fluid, bladder washings, secretions (e.g. breast secretion), oral washings, tissue samples, touch preps, or fine-needle aspirates. The type of biological sample that is used in the methods described herein depends on the type of cancer one wishes to detect. For example, urine and bladder washings provide useful biological samples for the detection of bladder cancer and to a lesser extent prostate or kidney cancer. Pleural fluid is useful for detecting lung cancer, mesothelioma or metastatic tumors (e.g. breast cancer), and blood is a useful biological sample for detecting leukemia. For tissue samples, the tissue can be fixed and placed in paraffin for sectioning, or frozen and cut into thin sections.

Typically, cells are harvested from a biological sample using standard techniques. For example, cells can be harvested by centrifuging a biological sample such as urine, and resuspending the pelleted cells. Typically, the cells are resuspended in phosphate-buffered saline (PBS). After centrifuging the cell suspension to obtain a cell pellet, the cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37–40% formaldehyde in an aqueous solution of sodium phosphate. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are resuspended in a final volume of about 100 to 200 $\mu$l of fixative. Three volumes of this suspension (usually 3, 10, and 30 $\mu$l), are then dropped into 6 mm wells of a slide. The cellularity (i.e. density of cells) in these wells is then assessed with a phase contrast microscope. If the well containing the greatest volume of cell suspension does not have enough cells, the cell suspension is concentrated and placed in another well.

Prior to in situ hybridization, chromosomal probes and chromosomal DNA contained within the cell each are denatured. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. Chromosomal probes can be denatured by heat. For example, probes can be heated to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. The higher the concentration of probe, the higher the probability of forming a hybrid. For example, in situ hybridizations are typically performed in hybridization buffer containing 1–2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 40° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

Chromosomal Probes

Suitable probes for in situ hybridization in accordance with the invention hybridize (i.e., form a duplex) with repetitive DNA associated with the centromere of a chromosome. Centromeres of primate chromosomes contain a complex family of long tandem repeats of DNA, composed of a monomer repeat length of about 171 base pairs, that is referred to as alpha-satellite DNA. Non-limiting examples of centromeric chromosomal probes include probes to chromosomes 3, 7, 8, 11, 15, 17, 18, and Y. Locus-specific probes that hybridize to a critical chromosomal region, such as the 9p21 region of chromosome 9, also are suitable.

Chromosomal probes are chosen for maximal sensitivity and specificity. Using a set of chromosomal probes (i.e., two or more probes) provides greater sensitivity and specificity than use of any one chromosomal probe. Thus, based on the results herein, chromosomal probes that detect the most frequently aneusomic chromosomes, and that complement each other, are included in a set. For example, based on discrimination values of probes determined herein, a set of chromosomal probes can include centromeric probes to chromosomes 3, 7, and 17. Additionally, the set can include probes to the 9p21 region of chromosome 9 or a centromeric probe to chromosome 8, chromosome 9, chromosome 11, or chromosome 18. As described herein, a probe to chromosome 7 when used alone demonstrated a high sensitivity, and could detect about 76% of bladder cancers. Probes to chromosomes 3 and 17, and to the 9p21 region of chromosome 9 were able to detect additional bladder cancer cases that showed no abnormality with chromosome 7 probe alone. The combination of probes to chromosomes 3, 7, 17, and to 9p21 provide a sensitivity of about 95% for detecting bladder cancer in the cohort of patients described herein.

Chromosomal probes are typically about 50 to about $1 \times 10^5$ nucleotides in length. Longer probes typically comprise smaller fragments of about 100 to about 500 nucleotides in length. Probes that hybridize with centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, *Biotechnic Histochem.*, 1998, 73(1): 6–22, Wheeless et al., *Cytometry* 1994, 17:319–326, and U.S. Pat. No. 5,491,224.

Chromosomal probes typically are directly labeled with a fluorophore, an organic molecule that fluorescesces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Fluorophores of different colors are chosen such that each chromosomal probe in the set can be distinctly visualized. For example, a combination of the following fluorophores may be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Probes are viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled with biotin or digoxygenin, or labeled with radioactive isotopes such as $^{32}P$ and $^{3}H$, although secondary detection molecules or further processing then is required to visualize the probes. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Selection of Cells

According to the invention, cells are microscopically selected from the cells of a biological sample (e.g. urine, etc.) on a slide prior to assessing if aneusomic cells are present or absent. "Selecting" refers to the identification of cells that are more likely to be neoplastic due to one or more cytologic (mainly nuclear) abnormalities such as nuclear enlargement, nuclear irregularity or abnormal nuclear staining (usually a mottled staining pattern). These nuclear features, can be assessed with nucleic acid stains or dyes such as propidium iodide or 4,6-diamidino-2-phenylindole dihydrochloride (DAPI). Propidium iodide is a red-fluorescing DNA-specific dye that can be observed at an emission peak wavelength of 614 nm. Typically, propidium iodide is used at a concentration of about 0.4 μg/ml to about 5 μg/ml. DAPI, a blue fluorescing DNA-specific stain that can be observed at an emission peak wavelength of 452 nm, generally is used at a concentration ranging from about 125 ng/ml to about 1000 ng/ml. Staining of cells with DAPI or propidium iodide is generally performed after in situ hybridization is performed.

Determining Presence of Aneusomic Cells

After a cell is selected based on one or more of the stated criteria, the presence or absence of aneusomy is assessed by examining the hybridization pattern of the chromosomal probes (i.e. the number of signals for each probe) in each selected cell, and recording the number of chromosome signals. This step is repeated until the hybridization pattern has been assessed in at least 4 cells, if all 4 cells are aneusomic. In a typical assay, the hybridization pattern is assessed in about 20 to about 25 selected cells.

Cells with more than two copies of multiple chromosomes (i.e., gains of multiple chromosomes) are considered cancer positive. Samples containing about 20 selected cells and at least about 4 test positive cells typically are considered cancer positive. If less than about 4 test positive cells are found, the level of chromosome ploidy is determined. A cancer positive result also is indicated if more than 30% of the cells demonstrate hemizygous or homozygous loss (i.e., nullisomy) of a specific chromosome region, such as loss of 9p21 in bladder cancer. Nullisomy can be confirmed as non-artifactual by observing the surrounding normal appearing cells to see if they have two signals for the specific chromosomal region.

Screening and Monitoring Patients for Cancer

The methods described herein can be used to screen patients for cancer, or can be used to monitor patients diagnosed with cancer. For example, in a screening mode, patients at risk for bladder cancer, such as patients older than 50 who smoke, or patients chronically exposed to aromatic amines, are screened with the goal of earlier detection of bladder cancer. The methods described herein can be used alone, or in conjunction with other tests, such as the hemoglobin dipstick test. For example, a patient having an increased risk of bladder cancer can be screened for bladder cancer by detecting hemoglobin in the urine, i.e., hematuria. During such a screening process, patients without hematuria do not need further analysis, and are instead, re-examined for hematuria in an appropriate amount of time, e.g., at their annual check-up. Samples from patients with hematuria are further analyzed using the methods described herein. In general, a set of chromosomal probes is hybridized with the biological sample, a subset of cells is selected, and the presence of aneusomic cells is determined in the selected cells. Patients that have aneusomic cells are further examined, for example, by cystoscopy, and can receive appropriate treatment, if necessary. After treatment, patients are monitored for cancer recurrence using the methods described herein.

The superior sensitivity of the methods described herein indicate that this technique could replace cytology for the detection and monitoring of cancers such as bladder cancer. The majority of patients with bladder cancer will have detectable aneusomic cells and can be monitored for treatment efficacy, and tumor recurrence/progression with the methods described herein. A small proportion of patients with cystoscopic or biopsy evidence of bladder cancer (primarily those with low grade non-invasive tumors) may not have detectable aneusomic cells in their urine. These patients (i.e. those with low grade papillary tumors) are at very low rate of tumor progression and may be conveniently monitored by a combination of the methods described herein and cystoscopy. The appearance of anuesomic cells in the urine of these patients may herald the development of a more aggressive tumor in this subset of patients. The high sensitivity and specificity of the FISH test described herein for aggressive bladder cancers may help reduce the frequency of cystoscopy.

The invention will be further described in the following examples, which do not limit the scope of the invention described in the claims.

EXAMPLES

Example 1

Samples and Sample Preparation

Samples included voided urine from 21 biopsy proven bladder cancer cases, in which a diagnosis was made by either positive cytology or by histology, in the case of cytology negative samples. Control urine samples included nine samples from normal healthy donors (age 25–80), and three samples from patients with genitourinary diseases other than bladder cancer.

Approximately 50 to 200 ml of urine were collected per patient. Urine samples were stored at 4° C. for less than 48 hours, and processed by centrifugation at 1200 g for 5 minutes. The supernatant was discarded, and the pellet resuspended in 10 ml of 0.075 M KCl, and incubated at room temperature for 15 minutes. Samples were spun for 5 minutes at 1200 g, and the KCl solution was removed. Pellets were resuspended in 10 ml of a 3:1 methanol:glacial acetic acid fixative, and centrifuged for 8 minutes at 1200 g. The fixative was carefully removed leaving the cell pellet, and this step was repeated two more times.

Density of the slides was monitored by frequently checking it under a phase contrast microscope, using a 20× objective, between droppings. Generally, it was attempted to obtain as many cells as possible on the slide without having any cell overlap. If a sample contained low numbers of cells, as much of the sample as possible was placed on the slide. In samples with very low numbers of cells, the whole sample was used. Slides were dried overnight at room temperature.

Slides containing the samples were incubated in 2×SSC at 37° C. for 10–30 minutes, then incubated in 0.2 mg/ml pepsin for 20 minutes at 37° C. Slides then were washed in PBS twice, for 2 minutes per wash, at room temperature. Cells were fixed in 2.5% Neutral Buffered Formalin for 5 minutes at room temperature. Slides again were washed in PBS twice, for 2 minutes per wash. After dehydration for 1 minute in each of 70%, 85%, and 100% ethanol, slides were used immediately, or stored at room temperature in the dark.

Three multicolor probe sets: A, B, and C were used in the initial hybridizations. Probe sets A–C contained the centromeric/locus specific probes shown in Table 1. The color of the fluorophore used to label each probe also is shown in Table 1. Chromosomal probes (CEP®, chromosomal enumeration probe) were obtained from Vysis, Inc. (Downers Grove, Ill.). An aqua filter was used to visualize chromosomes 17 and 18. A yellow filter was used to visualize the 9p21 locus specific probe, and a dual red/green filter or individual red or green filters were used to visualize chromosomes 3, 7, 8, 9, 11, and Y.

TABLE 1

FISH Probe Sets

| Probe Set | Spectrum Aqua | Spectrum Green | Spectrum Red | Spectrum Gold |
|---|---|---|---|---|
| A | 17 | 7 | 9 | 9p21 |
| B | 18 | 8 | 11 | |
| C | | 3 | Y | |

Hybridization was performed by a HYBrite method or a conventional method. In the HYBrite method, a HYBrite™ system from Vysis, Downers Grove, Ill., was used. Slides were placed on the HYBrite, and about 10 μl of the probe set were added, covered, and sealed. The HYBrite was programmed as follows: 73° C. for 5 min, then 37° C. for 16 hours. Slides then were washed in 0.4×SSC (0.06 M sodium chloride/0.006 M sodium citrate)/0.3% NP-40 for 2 minutes at 73° C., rinsed in 2×SSC/0.1% NP40 at room temperature, and air dried. Slides were counterstained with approximately 10 µl of DAPI II (125 ng/ml of 4,6-diamidino-2-phenylindole dihydrochloride).

In the conventional method (i.e., Coplin jar method), a master mix containing chromosome probes was prepared in hybridization buffer containing 50% formamide, 2×SSC, 0.5 µg/ml Cot1 DNA, and 2 µg/ml HP DNA. The probe mix was denatured at 73° C. for 5 minutes, and slides were denatured in denaturation buffer (70% formamide, 2×SSC) in a Coplin jar at 73° C. for 5 min (6–8 slides/jar). Slides were rinsed in each of 70%, 85%, and 100% ethanol for 1 minute. Approximately 10 µl of hybridization mix were applied to each slide, covered with a coverslip, and sealed with rubber cement. Hybridization was performed in a humidified chamber overnight at 37° C. Slides were washed in 0.4×SSC/0.3% NP-40 at 73° C. for 2 minutes, then rinsed in 2×SSC/0.1% NP-40 briefly at room temperature. After air drying, slides were counterstained with DAPI II. Samples were enumerated by recording the number of FISH signals in 100 consecutive cells.

In summary, this Example provides methods for isolating cells from a biological sample, and hybridizing a set of chromosomal probes to the cells.

Example 2
Detection of Bladder Cancer

Table 2 provides a summary of samples analyzed via cytology. Overall, urine cytology was positive in 13 out of 21 cancer cases, equaling a sensitivity of 62%. This value is consistent with published literature. Cytology detected tumor cells in 10 out of 11 bladder cancer patients with advanced stages of the disease (first 11 entries in Table 2). Among 10 patients with superficial bladder cancer (last 10 entries in Table 2), cytology was positive for 3 patients, equivocal for 3 patients, and negative for 4 patients. ND refers to non-determined. Equivocal (E) refers to samples that were suspicious, but not diagnostic of transitional cell carcinoma (TCC). pTis refers to carcinoma in situ, and pTa refers to non-invasive papillary carcinoma. pT1 refers to invasion of subepithelial connective tissue by the tumor; pT2 refers to invasion of muscle by the tumor; pT3 refers to invasion of perivesical tissue by tumor; and pT4 refers to invasion of the prostate, uterus, vagina, pelvic wall, or abdominal wall.

The percent of aneusomic cells with four or more chromosome signals permitted the greatest discrimination between the cancer group and normal cases. Single copy gains or losses among the control group showed much higher frequencies and did not result in comparable sensitivities and specificities. The percentage of aneusomic cells, using this definition, was determined for each group of samples (cancer and normal) and individually in each group. Using this definition, samples were analyzed in the following manner.

Discriminate analysis was performed to determine how well each probe differentiated cancer cases from normal control, using the formula $$\text{Discrimination Value} = \frac{(M1 - M2)^2}{SD1^2 + SD2^2}$$

In this formula, M1 and M2 are the mean percent aneusomic cells with four or more signals for cancer (n=21) and normal (n=9) groups, respectively, and SD1 and SD2 are standard deviations for each group of samples. Table 3 provides a summary of the results for the chromosome enumeration probes (CEP) using this analysis.

TABLE 2

Detection of Bladder Cancer Via Cytology

| Patient | Status | Stage | Grade | Cytology |
|---------|--------|-------|-------|----------|
| 215 | Cancer | ND | ND | positive |
| 219 | Cancer | pT3 | 3 | positive |
| 224 | Cancer | pTis | 3 | positive |
| 228 | Cancer | ND | ND | ND |
| 236 | Cancer | pTis | 3 | positive |
| 66 | Cancer | pT3 | 3 | positive |
| D | Cancer | ND | ND | positive |
| 229 | Cancer | pT3 | 3 | positive |
| 171 | Cancer | pT4 | 3 | positive |
| 227 | Cancer | pT4 | 3 | positive |
| 240 | Cancer | pT3 | 3 | negative |
| 191 | Cancer | pTa | 2 | positive |
| 225 | Cancer | pTa | 2 | positive |
| 230 | Cancer | pTa | 3 | positive |
| 223 | Cancer | pTa | 2 | E |
| 234 | Cancer | pTa | 2 | E |
| 235 | Cancer | pTa | 2 | E |
| 239 | Cancer | pTa | 3 | negative |
| 69 | Cancer | pTa | 2 | negative |
| 110 | Cancer | pT1 | 3 | negative |
| 95 | Cancer | pT1 | 3 | negative |

TABLE 3

Probe Discrimination Values

|  | CANCER | NORMAL |
|---|--------|--------|
| Mean CEP 17 | 24.77 | 0.89 |
| SD (CEP 17) | 25.44 | 1.76 |
| Discrimination | 0.88 | |
| Mean CEP 9 | 15.55 | 1.07 |
| SD (CEP 9) | 19.33 | 2.01 |
| Discrimination | 0.55 | |
| Mean CEP 7 | 26.58 | 1.07 |
| SD (CEP 7) | 24.12 | 1.82 |
| Discrimination | 1.11 | |
| Mean CEP 18 | 13.09 | 1.63 |
| SD (CEP 18) | 14.35 | 1.80 |
| Discrimination | 0.63 | |
| Mean CEP 11 | 16.32 | 1.52 |
| SD (CEP 11) | 19.44 | 1.87 |
| Discrimination | 0.57 | |
| Mean CEP 8 | 15.58 | 1.52 |
| SD (CEP 8) | 15.47 | 1.87 |
| Discrimination | 0.81 | |
| Mean CEP 3 | 27.91 | 0.49 |
| SD (CEP 3) | 26.33 | 0.78 |
| Discrimination | 1.08 | |

A discrimination value of >1.0, the 95% confidence interval around which two populations are separated, was considered good. (assuming normal distribution and roughly equivalent standard deviation values). By this criteria, the best probes were 7, 3, and 17. This analysis provides information regarding the sensitivity and specificity of individual probes but does not reveal the sensitivity/specificity of different probe combinations.

A cutoff of two standard deviations above the mean % of aneusomic cells in normal cells was used as the criterion of FISH positivity for chromosomal gains. On the other hand, 9p21 changes in bladder cancer are manifested as a loss and thus were evaluated as nullisomy. The cutoff value used for nullisomy was 3 standard deviations greater than the mean of normal samples. The percent aneusomic cells for each case by probe are shown in Table 4A for normal individuals and in Table 4B for cancer patients. In Table 4B, samples below the double line are cytology false negative cases, and shaded text indicates false negative FISH results using the cutoff values from Table 3. As shown in Table 4A, the percent of aneusomic cells (as defined by chromosomal gains) in normal samples is low, ranging from about 0.5% to about 4.5%.

TABLE 4A

Percent of aneusomic cells: normal cases

| Patient | CEP 17 | CEP 9 | CEP 7 | CEP 18 | CEP 11 | CEP 8 | CEP 3 | 9p21 |
|---|---|---|---|---|---|---|---|---|
| 2F | 0 | 0 | 0 | 0 | 0 | 0 | 0 | 0 |
| 3M | 0 | 0 | 0 | 0 | 0 | 0 | 0 | 1.00 |
| 8M | 0 | 0 | 0 | 0 | 0 | 0 | 0 | 0 |
| 9M | 0 | 0 | 0 | 5 | 4 | 5 | 1 | 3.00 |
| F5 | 4 | 2 | 2 | 2 | 1 | 1 | 0 | ND |
| F6 | 0 | 6 | 0 | 0 | 0 | 0 | 1.43 | 0 |
| M12 | 4 | 1.67 | 6 | 3 | 5 | 4 | 2.00 | 14.00 |
| M28 | 0 | 0 | 1.67 | 1.67 | 1.67 | 1.67 | 0 | 3.33 |
| M23 | 0 | 1.07 | 0 | 3 | 2.00 | 2.00 | 0 | 15.00 |
| MEAN | 0.88 | 1.81 | 1.07 | 1.63 | 1.51 | 1.51 | 0.49 | 4.54 |
| SD | 1.76 | 2.01 | 1.81 | 1.79 | 1.87 | 1.87 | 0.77 | 6.29 |
| Mean + 2D | 4.41 | 5.09 | 4.7 | 5.2 | 5.26 | 5.26 | 2.05 | 17.12 |

TABLE 4A

Percent of aneusomic cells: normal cases

| Patient | CEP 17 | CEP 9 | CEP 7 | CEP 18 | CEP 11 | CEP 8 | CEP 3 | Null 9p21 |
|---|---|---|---|---|---|---|---|---|
| 171 | 21 | 0 | 24 | 2 | 42 | 44 | 1 | 9 |
| 191 | 3.45 | 10.34 | 17.24 | 44.9 | 26.53 | 38.78 | 50 | 4.76 |
| 215 | 38 | 21 | 24 | 5.81 | 4.65 | 2.33 | 60.32 | 13 |
| 219 | 39 | 44 | 41 | 14 | 11 | 24 | 53 | 10 |
| 224 | 73.68 | 70.3 | 81.05 | ND | ND | ND | ND | 69.47 |
| 225 | 5 | 4 | 9 | 5 | 12 | 6 | 20 | 16 |
| 227 | 52 | 33 | 69 | 37 | 14 | 34 | 44 | 1 |
| 228 | 34 | 13 | 29 | 32 | 2 | 34 | 53 | 3 |
| 229 | 3 | 20 | 35 | 5 | 47 | 8 | 43 | 4 |
| 230 | 38 | 39 | 32 | 13 | 8 | 9 | 44 | 8 |
| 236 | 50 | 17 | 49 | 21 | 34 | 35 | 54 | 62 |
| 66 | 84 | 5 | 66 | 36 | 70 | 7 | 78.89 | 27 |
| D | 41.94 | 38.71 | 38.71 | ND | ND | ND | ND | 12.9 |
| 239 | 0 | 0 | 0 | 3 | 4 | 4 | 0 | 20 |
| 240 | 5 | 0 | 13 | 18 | 23 | 32 | 0 | 1 |
| 69 | 2 | 1 | 2 | 0 | 0 | 0 | 5 | 2 |
| 95 | 0 | 0 | 0 | 2 | 2 | 2 | 0 | 2 |
| 110 | 10.1 | 1 | 18.18 | 3 | 2 | 6 | 11 | 20.2 |
| 223 | 0 | 0 | 0 | 3 | 5 | 7 | 0 | 43 |
| 234 | 11 | 9 | 9 | 3 | 2 | 2 | 3 | 3 |
| 235 | 9 | 0 | 1 | 1 | 1 | 1 | 10 | 1 |

TABLE 5

Results of FISH and Cytology for Normal and Bladder Cancer Patients

| | Bladder Cancer (n = 21) | | Non Cancer (n = 3) |
|---|---|---|---|
| | Cytology+ | Cytology− | Cytology− |
| FISH + | 13 | 7 | 0 |
| FISH − | 0 | 1 | 3 |

Overall, as shown in Table 4B, chromosome 7 demonstrated the highest sensitivity of any individual probe (76%, 16/21). Probes to chromosome 3 and 9p21 complemented chromosome 7 in that they were positive for some of the cases with normal chromosome 7 results. In combination, the three probes to chromosomes 3, 7 and 9p21 detected 20/21 bladder cancer cases and more importantly 7/8 cytology false negative cases (Table 4B). In this data set, this equates to an overall sensitivity of 95%.

The chromosome 17 probe (along with the chromosome 3 probe) detected the highest number of cytology false-negative samples (4/8).

Example 3

Comparative Analysis with Standard Screening Methods 190 patients from the Mayo clinic were prospectively enrolled in this study. A majority of the patients either had a previous diagnosis of bladder cancer or were being evaluated for a possible initial diagnosis of bladder cancer (e.g. for microhematuria). A small proportion of the patients were being evaluated for genitourinary disorders other than bladder cancer. Test methodologies compared included urine cytology, cystoscopy, BTA STAT (C. R. Bard, Inc., Murray Hill, N.J.), FISH, and hemoglobin dipstick (Bayer Corporation, Diagnostic Division, Elkhart, Ind.).

FISH generally was performed as described in Example 1. Approximately 25 to 200 ml of urine were collected per patient. Urine samples were stored at 4° C. for up to 48 hours, and processed by centrifugation at 600 g for 10 minutes. The supernatant. was discarded, and the pellet was resuspended in 25–50 ml of 1× phosphate-buffered saline (PBS). After centrifugation for 5 minutes at 600 g, the supernatant again was discarded. Pellets were resuspended slowly in 1.5–5 ml of fixative (methanol:glacial acetic acid, 3:1), and centrifuged for 5 minutes at 600 g. The fixative was carefully removed, and this step was repeated two more times.

After the final centrifugation, the fixative was removed, leaving an appropriate amount of the solution for dropping onto slides such as the 12-Circle 6 mm Shandon Lipshaw slides. If the cell pellet was very small, and hardly visible to the eye, approximately 100 $\mu$l were left above the pellet. If the cell pellet was easily visible by eye, as much Carnoy's fixative as possible was removed, and 0.5 ml of fresh Carnoy's fixative was added. If no pellet was visible, the entire sample often was dropped on one slide. Approximately 3, 10, and 30 $\mu$l of the cell suspension were then dropped into three separate 0.6 mm wells of a Shandon 12 well slide. The cellularity (i.e. density of cells) in these wells was assessed with a phase contrast microscope. If the well containing the smallest volume of cell suspension is too dense, the cell suspension is further diluted and a portion of this dilution is put in a fourth well. If the well containing the greatest volume of cell suspension does not have enough cells, the cell suspension is concentrated and placed in a fourth well.

Slides containing the samples were incubated in 2×SSC at 37° C. for 10–30 minutes, then incubated in 0.2 mg/ml pepsin for 10 minutes at 37° C. Slides then were washed in PBS twice, for 2 minutes per wash, at room temperature. Cells were fixed in 2.5% Neutral Buffered Formalin for 5 minutes at room temperature. Slides again were washed in PBS for 5 minutes. After dehydration for 1 minute in each of 70%, 85%, and 100% ethanol, slides were dried on a slide warmer at 45–50° C. for 2 minutes. Slides were either left in 100% ethanol at 4° C. until further use, or were used for FISH.

Hybridization was performed by a HYBrite method or a conventional method. In the HYBrite method, a HYBrite™ system from Vysis, Downers Grove, Ill., was used. Slides were placed on the HYBrite, and about 3 $\mu$l of probe were added per target, then the slides were covered and sealed. The HYBrite was programmed as follows: 73° C. for 5 min, then 37° C. for 16 hours. Slides then were washed in 0.4 SSC (0.06 M sodium chloride/0.006 M sodium citrate)/0.3% NP-40 for 2 minutes at 73° C., rinsed in 2×SSC/0.1% NP40 at room temperature, and air dried. Slides were counterstained with approximately 3 μl of DAPI II (125 ng/ml of 4,6-diamidino-2-phenylindole dihydrochloride).

In the conventional method, a master mix containing chromosome probes was prepared in hybridization buffer containing 50% formamide, 2×SSC, 0.5 μg/ml Cot1 DNA, and 2 μg/ml HP DNA. The probe mix was denatured at 73° C. for 5 minutes, and slides were denatured in denaturation buffer (70% formamide, 2×SSC) in a Coplin jar at 73° C. for 5 min (6–8 slides/jar). Slides were rinsed in each of 70%, 85%, and 100% ethanol for 1 minute. Samples were dried on a slide warmer for 2 minutes or less. Approximately 3 μl of hybridization mix were applied per target on each slide, and the slides were covered immediately with a coverslip, which then was sealed with rubber cement. Hybridization was performed in a humidified chamber overnight at 37° C. Slides were washed in 0.4×SSC/0.3% NP-40 at 73° C. for 2 minutes, then rinsed in 2×SSC/0.1% NP-40 briefly at room temperature. After air drying, slides were counterstained with DAPI II. Twenty cytologically abnormal cells were selected in each sample, and analyzed for their FISH pattern.

For 53 cancer cases, as diagnosed by biopsy (Stage/Grade) (n=49) and cytology positive TCC (n=34), cytology had a sensitivity of 57% (equivocal cytology diagnoses counted as positive), cystoscopy had a sensitivity of 88% (equivocal cystoscopy results counted as positive), BTA STAT had a sensitivity of 71%, and FISH had a sensitivity of 86%. In 63 cancer negative cases, as indicated by a negative cystoscopy with or without negative cytology and no history of bladder cancer, BTA STAT had a specificity of 73%, and FISH had a specificity of 90% (specificity of cystoscopy and cytology cannot be determined since they were used to define which patients did not have bladder cancer.

Two of the three patients with "false positive" FISH results also had positive telomerase, hemoglobin dipstick and BTA-STAT or BTA-TRAK results. Should these two patients prove to have bladder cancer, the specificity of FISH will approach 100%. This has implications for the positive predictive value of the test as discussed below. Table 6 shows the sensitivity of the various tests by stage and grade. In Table 6, "E" refers to equivocal, and "*" indicates 3 FISH+ samples were cancer by cytology only and were not included.

The positive and negative predictive values (PV), based on a disease prevalence of 28% (53/190), specificity of 93% and sensitivity of 77%, are indicated in Table 7.

TABLE 6

|  | Grade 1 | Grade 2 | Grade 3 | Overall |
|---|---|---|---|---|
| Cytology |  |  |  |  |
| pTa | 1 + [1E]/8 | 5/13 | 2/2 | 39% (9/23) |
| pT1–pT4 |  |  | 3 + [3E]/9 | 66% (6/9) |
| pTis |  |  | 5 + [5E]/12 | 83% (10/12) |
| Overall | 25% (2/8) | 38% (5/13) | 78% (18/23) | 57% (25/44) |
| Cystoscopy |  |  |  |  |
| pTa | 5 + [1E]/7 | 13/13 | 2/2 | 95% (21/22) |
| pT1–pT4 |  |  | 4 + [3E]/9 | 78% (7/9) |
| pTis |  |  | 5 + [5E]/12 | 83% (10/12) |
| Overall | 86% (6/7) | 100% (13/13) | 83% (19/23) | 88*% (38/43) |
| FISH |  |  |  |  |
| pTa | 4/7 | 9/12 | 2/2 | 71% (15/21) |
| pT1–pT4 |  |  | 12/12 | 100% (12/12) |
| pTis |  |  | 10/10 | 100% (10/10) |
| Overall | 57% (4/7) | 75% (9/12) | 100% (24/24) | 86*% (37/43) |
| BTA |  |  |  |  |

TABLE 6-continued

|  | Grade 1 | Grade 2 | Grade 3 | Overall |
|---|---|---|---|---|
| STAT |  |  |  |  |
| pTa | 4/8 | 6/14 | 2/2 | 50% (12/24) |
| pT1–pT4 |  |  | 9/10 | 90% (9/10) |
| pTis |  |  | 12/12 | 100% (12/12) |
| Overall | 50% (4/8) | 43% (6/14) | 96% (24/25) | 71% (33/46) |

TABLE 7

| | Predictive Value | |
|---|---|---|
| Method | PV+ | PV− |
| FISH | 77% | 94% |
| BTA STAT | 51% | 87% |

Fifty-one out of the 53 cancer cases had a dipstick result. The sensitivity of the hemoglobin dipstick test was 91% for stages pT1–pT4 and 100% for carcinoma in situ (Tis), making it an ideal screening test (Table 8). However, the specificity (52%) of the hemoglobin dipstick test was poor. While the high sensitivity and low cost of the hemoglobin dipstick make it a useful screening test, it is clear that positive results must be confirmed by a more specific test. Cytology cannot be the test of choice because it detected as positive only 33% of pT2–pT4 cases and missed 2 of 12 carcinoma in situ (see Table 6).

TABLE 8

| | Hb dipstick | | |
|---|---|---|---|
| | Trace to 3+ | Negative | Sensitivity |
| pTa | 13 | 11 | 54% |
| pT1–pT4 | 10 | 1 | 91% |
| pTis | 12 | 0 | 100% |

The clinical utility of FISH was compared to the standard cytology/cystoscopy testing regimen. Of the 53 cancer cases, there were 22 cases of advanced stage disease (pT2–pT4 or pTIS). Failure to detect these cases represents the most serious false negative situation. While cytology/cystoscopy was positive in 13/22 cases for a sensitivity of 59%, FISH had 100% sensitivity, i.e., was able to detect 22/22 cases (see Table 9 for a representation of 5 of these cases). This indicates that FISH is an improved cytology test which has high sensitivity for detecting advance stages of disease.

TABLE 9

| Patient | Stage | Grade | Cystoscopy | Cytology | FISH |
|---|---|---|---|---|---|
| 79 | pT2 | Grade 3 | E | E | Pos |
| 132 | pT2 | Grade 3 | Neg | Neg | Pos |
| 1 | pT3 | Grade 3 | Neg | Neg | Pos |
| 115 | pT4 | Grade 3 | E | E | Pos |
| 180 | pTIS | Grade 3 | E | Neg | Pos |

Other Embodiments

It is understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of screening for cancer in a subject comprising:
   (a) hybridizing a set of chromosomal probes to a biological sample from said subject, wherein said set comprises at least three chromosomal probes selected from the group consisting of probes to chromosomes 3, 7, 8, 9, 11, 15, 17, 18, and Y;
   (b) selecting cells from said biological sample; and
   (c) determining the presence or absence of aneusomic cells in said selected cells by examining the hybridization pattern of said set of chromosomal probes in each of said selected cells, wherein the presence of aneusomic cells in said selected cells is indicative of cancer in said subject.

2. The method of claim 1, wherein said biological sample is selected from the group consisting of urine, blood, cerebrospinal fluid, pleural fluid, sputum, peritoneal fluid, bladder washings, oral washings, tissue samples, touch preps, and fine-needle aspirates.

3. The method of claim 1, wherein said biological sample is concentrated.

4. The method of claim 1, wherein said biological sample is urine.

5. The method of claim 1, wherein said cancer is selected from the group consisting of bladder cancer, lung cancer, breast cancer, ovarian cancer, prostate cancer, colorectal cancer, renal cancer, and leukemia.

6. The method of claim 1, wherein said cancer is bladder cancer.

7. The method of claim 1, wherein said chromosomal probes are fluorescently labeled.

8. The method of claim 1, wherein said set comprises at least one centromeric probe.

9. The method of claim 8, wherein said set further comprises at least one locus specific probe.

10. The method of claim 8, wherein said centromeric chromosomal probes are selected from the group consisting of probes to chromosomes 3, 7, 8, 11, 15, 17, 18, and Y.

11. The method of claim 9, wherein said locus specific probe is to the locus 9p21.

12. The method of claim 1, wherein said set comprises probes to chromosomes 3, 7, and 17.

13. The method of claim 12, wherein said set further comprises a locus specific probe to the locus 9p21.

14. The method of claim 1, wherein cells are selected by nuclear morphology.

15. The method of claim 1, wherein cells are selected by nuclear size.

16. The method of claim 1, wherein cells are selected by shape of nucleus.

17. The method of claim 14, wherein nuclear morphology is assessed by DAPI staining.

* * * * *